United States Patent [19]
Burns

[11] Patent Number: 5,476,477
[45] Date of Patent: Dec. 19, 1995

[54] INNERLESS CATHETER

[75] Inventor: Matthew M. Burns, Minneapolis, Minn.

[73] Assignee: SciMed Lift Systems, Inc., Minneapolis, Minn.

[21] Appl. No.: 321,161

[22] Filed: Oct. 11, 1994

Related U.S. Application Data

[63] Continuation of Ser. No. 13,149, Feb. 1, 1993, abandoned, which is a continuation of Ser. No. 730,224, Jul. 15, 1991, abandoned, which is a continuation of Ser. No. 337,272, Apr. 13, 1989, Pat. No. 5,032,113.

[51] Int. Cl.⁶ .......................... A61M 29/02; A61M 25/00
[52] U.S. Cl. .......................... 606/194; 606/192; 604/96; 604/264
[58] Field of Search .................. 604/96–97, 101–103, 604/264, 280; 606/191–192, 194–195

[56] References Cited

U.S. PATENT DOCUMENTS

| | | | |
|---|---|---|---|
| 4,456,000 | 6/1984 | Schjeldahl et al. | 606/194 |
| 4,606,347 | 8/1986 | Fogarty et al. | 604/167 |
| 4,646,742 | 3/1987 | Packard et al. | 604/102 |
| 4,762,129 | 8/1988 | Bonzel | 604/96 |
| 4,782,834 | 11/1988 | Maguire et al. | 604/280 |
| 4,811,737 | 3/1989 | Rydell | 606/194 |
| 4,819,630 | 4/1989 | Dehart | 606/16 |
| 4,820,262 | 4/1989 | Finney | 604/281 |
| 4,820,349 | 4/1989 | Saab | 604/96 |
| 4,846,174 | 7/1989 | Willard et al. | 604/96 |
| 4,848,344 | 7/1989 | Sos et al. | 604/96 |
| 4,877,031 | 10/1989 | Conway et al. | 604/96 |
| 4,917,666 | 4/1990 | Solar et al. | 606/194 |
| 4,955,895 | 9/1990 | Sugiyama et al. | 606/194 |
| 5,002,532 | 3/1991 | Gaiser et al. | 606/194 |
| 5,032,113 | 7/1991 | Burns | 604/280 |
| 5,035,705 | 7/1991 | Burns | 606/194 |
| 5,135,487 | 8/1992 | Morrill et al. | 606/194 |
| 5,171,222 | 12/1992 | Euteneuer et al. | 606/194 |

Primary Examiner—Stephen C. Pellegrino
Assistant Examiner—Nancy Mulcare
Attorney, Agent, or Firm—Nawrocki, Rooney & Sivertson

[57] ABSTRACT

An over-the-wire balloon catheter for use in angioplasty includes a proximal single lumen shaft and a multilumen distal portion on which an inflatable balloon is mounted. The lumen of the shaft acts as a combined inflation lumen and guide wire lumen. In the multilumen distal portion, a distal inflation lumen connects the combined lumen with the interior of the balloon, while the distal guide wire lumen extends through the balloon to provide a passage for a guide wire.

3 Claims, 4 Drawing Sheets

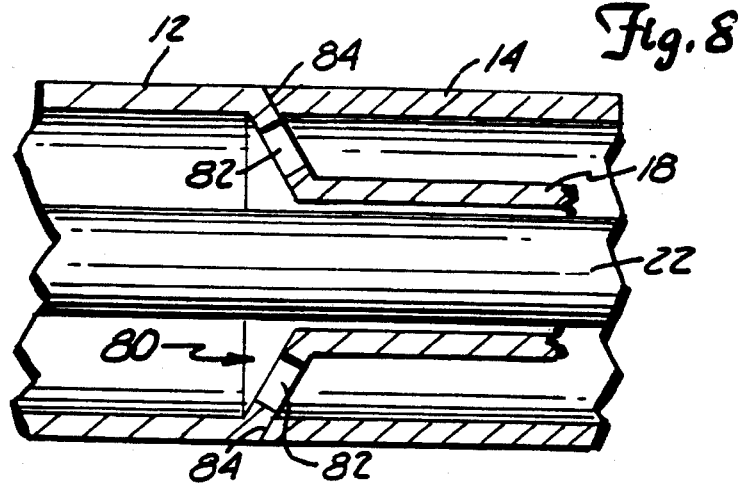
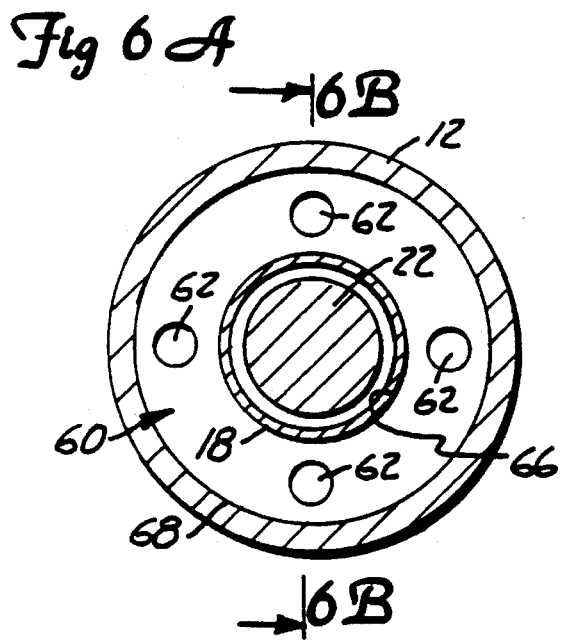
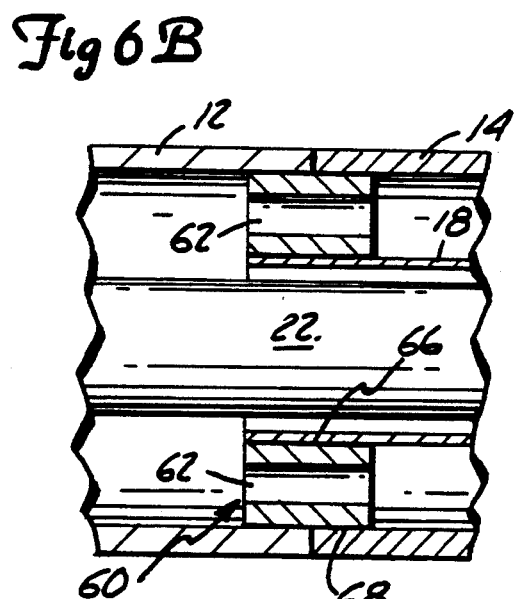
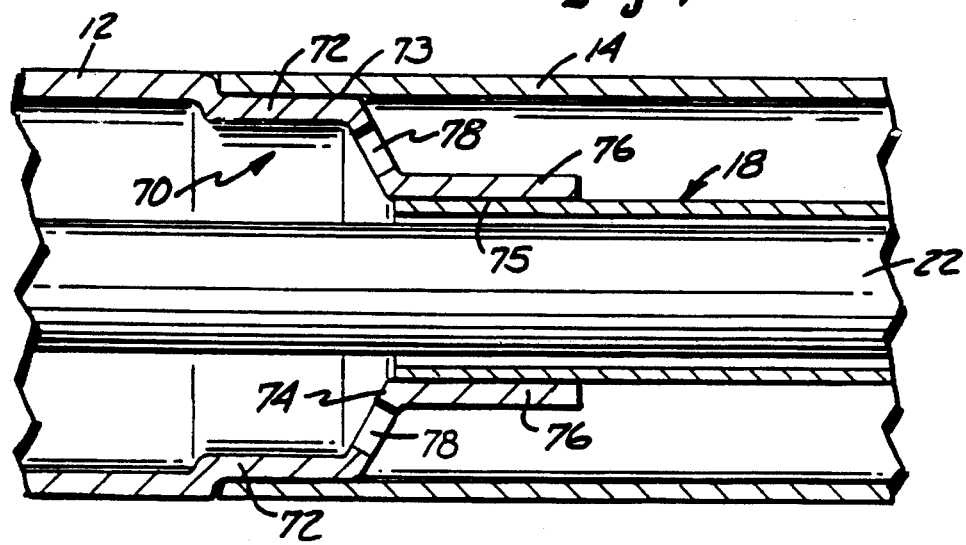

INNERLESS CATHETER

CROSS REFERENCE TO CO-PENDING APPLICATIONS

This application is a continuation of U.S. Ser. No. 08/013,149, filed Feb. 1, 1993, entitled "Innerless Catheter", now abandoned, which is a continuation of U.S. Ser. No. 07/730,224, filed Jul. 15, 1991, entitled "Innerless Catheter" now abandoned, which is a continuation of U.S. Ser. 07/337,272 filed Apr. 13, 1989, now U.S. Pat. No. 5,032,113.

BACKGROUND OF THE INVENTION

1. Field of the Invention

The present invention relates to the field of angioplasty. In particular, the present invention relates to a dilatation balloon catheter.

2. Description of the Prior Art

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. The inflation of the balloon causes stretching of the artery and pressing of the lesion into the artery wall to reestablish acceptable blood flow through the artery.

There has been a continuing effort to reduce the profile and improve the trackability (flexibility) of the dilatation catheter so that the catheter can not only reach, but also cross a very tight stenosis. A further requirement of a successful dilatation catheter is its "pushability". This involves the transmission of longitudinal force along the catheter from its proximal end to its distal end so that a physician can push the catheter through the vascular system and the stenosis.

Two types of dilatation catheters are "over-the-wire" catheters and "non-over-the-wire" catheters. An over-the-wire catheter is one in which a separate guide wire lumen (sometimes called a "thru lumen") is provided so that a guide wire can be used to establish the path through the stenosis. The dilatation catheter can then be advanced over the guide wire until the balloon is positioned within the stenosis. One problem with the over-the-wire catheter is the requirement of a larger profile and a generally larger outer diameter along its entire length in order to allow for a separate guide wire lumen.

A non-over-the-wire catheter acts as its own guide wire, and thus there is no need for a separate guide wire lumen. One advantage of a non-over-the-wire catheter is its potential for reduced profile since a guide wire lumen is not required. However, one disadvantage is the inability to maintain the position of a guide wire within the vascular system when removing the catheter and exchanging it for one of a smaller (or larger) balloon diameter. Thus, to accomplish an exchange with the non-over-the-wire catheter, the path to the stenosis must be reestablished when replacing the catheter with one having a different balloon diameter.

SUMMARY OF THE INVENTION

The catheter of the present invention includes a main shaft, a secondary distal outer tube connected to the main shaft at the distal end of the main shaft, a distal inner tube extending through the distal outer tube, an inflatable balloon, which is attached at its proximal end to the distal outer tube and at its distal end to the distal inner tube. The main shaft is an elongate hollow thin-walled metal tube having a proximal end and a distal end, and having a lumen extending therethrough from the proximal end to the distal end which functions as both an inflation lumen and a guide wire lumen. A distal inflation lumen is defined between the distal outer tube and the distal inner tube and is in fluid communication with the combined inflation/guide wire lumen of the main shaft and with the interior of the balloon. The distal inner tube has a distal guide wire lumen which is aligned with the combined lumen of the main shaft and extends through the balloon to provide a passageway for a guide wire.

In preferred embodiments an insert provides a fluid path between the combined lumen and the distal inflation lumen, and provides a platform for connecting the main shaft to the distal inner and outer tubes.

The resistance to fluid flow between the combined lumen and the interior of the balloon is substantially less than the resistance to fluid flow between an outer surface of the guide wire and an inner surface of the distal inner tube. This resistance to fluid flow effectively provides an essentially fluid-tight seal between the inner surface of the distal inner tube and the outer surface of the guide wire when positive or negative fluid pressure is applied to the interior of the balloon.

In one preferred embodiment of the present invention, the insert comprises a main insert tube having a length substantially shorter than that of the distal outer tube and having a plurality of smaller diameter openings (e.g., small tubes) disposed evenly about the main insert tube for providing a fluid path between the combined lumen and the distal inflation lumen. The plurality of small tubes are bonded to an outer surface of the main insert tube.

In another preferred embodiment of the present invention, the insert comprises an insert tube having a proximal end with a larger diameter than a distal end thereof, and having radial perforations in the walls of the insert tube for providing a fluid path between the combined lumen of the main shaft and the distal inflation lumen.

In another preferred embodiment of the present invention, the insert comprises an insert tube of uniform diameter having tubular slots within the walls of the insert tube extending throughout the length of the insert tube for providing a fluid path between the combined lumen and the distal inflation lumen.

In another preferred embodiment of the present invention, the insert is integral with, and of similar construction to, the main shaft and has a smaller outer diameter than the main shaft. The insert has radial perforations in its walls for providing a fluid path between the combined lumen and the distal inflation lumen. The insert has a smaller diameter at a distal end thereof and has the proximal end of the distal inner tube member bonded to either an inner surface or an outer surface at the distal end of the insert.

In another preferred embodiment of the present invention, the means for providing a fluid path between the combined lumen and the distal inflation lumen comprises perforations located in the walls of a distal end portion of the main shaft. The distal end portion of the main shaft is integral with and of similar construction to the distal inner tube, and the distal end of the main shaft has a smaller diameter than the proximal end.

In another preferred embodiment of the present invention, the insert comprises a tubular-shaped member having walls comprised of a permeable material such that the walls of the tubular-shaped member act as a fluid path between the combined lumen and the distal inflation lumen.

In another preferred embodiment of the present invention, the insert comprises a tubular-shaped member having a multiple ribbed outer surface which forms cavities that act as a fluid path between the combined lumen and the distal inflation lumen.

In another preferred embodiment of the present invention, the insert comprises a member having a single ribbed outer surface which forms a pair of grooves acting as a fluid path between the combined lumen and the distal inflation lumen.

In another preferred embodiment of the present invention, the insert comprises a tubular-shaped member having a multiple ribbed inner surface which forms cavities between the tubular-shaped member and the distal inner tube which act as a fluid path between the combined lumen and the distal inflation lumen.

In another preferred embodiment of the present invention, the insert comprises a tubular-shaped member having a single ribbed inner surface which forms a pair of grooves between the tubular-shaped member and the distal inner tube which act as a fluid path between combined lumen and the distal inflation lumen.

Preferably, the insert of the present invention facilitates the introduction of a distal end of the guide wire from the combined lumen into a proximal end of the distal inner tube. To this end, the insert may include a diametrically sloped guide wire transition guiding surface to direct the distal end of the guide wire into the proximal end of the distal inner tube.

BRIEF DESCRIPTION OF THE DRAWINGS

FIG. 6A is a detail lateral sectional view of an insert which is another preferred embodiment of the balloon catheter of the present invention.

FIG. 6B is a sectional view along lines 6B—6B in FIG. 6A.

FIG. 7 is a detail sectional view of an insert which is another preferred embodiment of the balloon catheter of the present invention.

FIG. 8 is a detail sectional view of another preferred embodiment of the balloon catheter of the present invention.

DETAILED DESCRIPTION OF THE PREFERRED EMBODIMENTS

Figure 1:
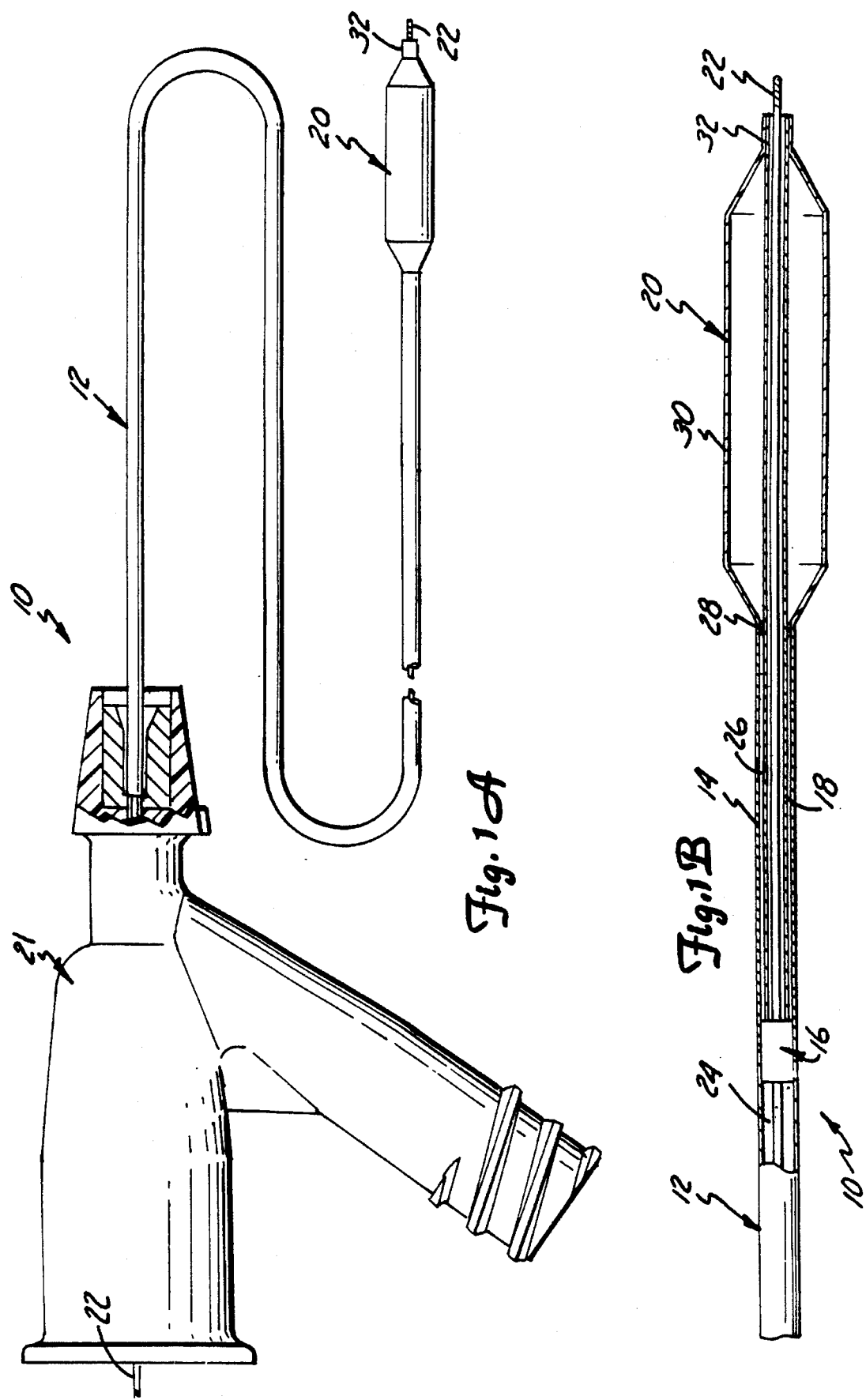
FIG. 1A shows a balloon catheter system of the present invention, with some parts broken away and shown in section.
FIG. 1B is an enlarged sectional view of the distal end of the balloon catheter of FIG. 1.

Dilatation balloon catheter 10 shown in FIGS. 1A and 1B includes main shaft 12, distal outer tube 14, insert or plug 16, distal inner tube 18, and balloon member 20. Connected at the proximal end of main shaft 12 is manifold 21, which is adapted to be connected to an inflation device (not shown) for inflating and deflating balloon 20. Guide wire 22 extends through manifold 21, main shaft 12, and distal inner tube 18, and out the distal end of catheter 10.

Main shaft 12 is an elongated flexible thin-walled tube, preferably of stainless steel or polyimide with a low friction coating such as PARALENE (poly p-xylyene), TELFON (PTFE fluorocarbon), or silicone rubber. In the embodiment shown in FIGS. 1A and 1B, main shaft 12 has an inside diameter of about 0.029 inch, and outside diameter of about 0.031 inch, and a shaft coating thickness of about 0.001 inch. Main shaft 12 is mounted at its proximal end to manifold 21 which is connected to an inflation device (not shown) to provide positive fluid pressure to lumen 24 of main shaft 12 for balloon inflation, and negative fluid pressure for balloon deflation. Of course, the manifold has a diaphragm or Touhy-Borst type fitting relative to the guide wire and proximal end of the manifold to permit selective closure of a hermetic seal about the guide wire when the combined lumen is inflated or deflated. Opening of the fitting permits guide wire movement, while closure thereof prevents fluid from escaping out of the manifold adjacent the proximal end thereof and the guide wire.

Mounted at the distal end of main shaft 12 is distal outer tube 14, which extends from the distal end of main shaft 12 to the proximal end of balloon member 20. Distal outer shaft 14 is a hollow, flexible, and preferably torque transmitting shaft which has greater flexibility than main shaft 12. Distal inflation lumen 26 (which is defined by the annular space between distal outer tube 14 and distal inner tube 18) is in fluid communication with lumen 24 of main shaft 12 and connects lumen 24 with the interior of balloon member 20.

Figure 2:
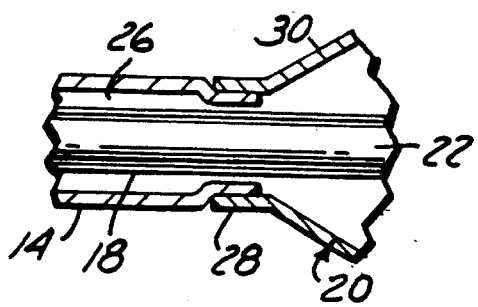
FIG. 2 is a detail sectional view of the inflatable balloon bonded to the distal outer tube of the balloon catheter of the present invention.

Balloon member 20, which is preferably a polymer material such as a polyolefin or polyimide, includes proximal bond segment 28, distensible balloon segment 30, and small diameter distal segment 32. FIG. 2 shows proximal bond segment 28 bonded to the distal end of distal outer tube 14.

FIG. 2 is a magnified view of a portion of FIG. 1B, showing in further detail distal outer shaft 14, distal inner shaft 18, guide wire 22, distal inflation lumen 26, proximal bond segment 28 of balloon member 20, and distensible balloon segment 30 of balloon member 20.

Figure 3:
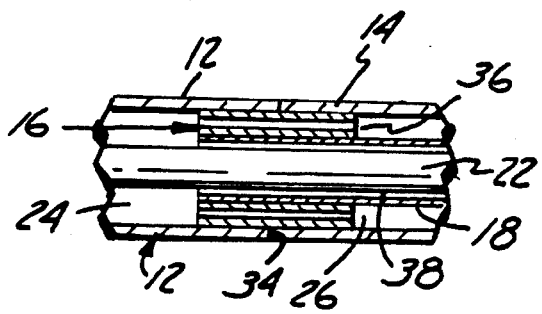
FIG. 3 is a detail sectional view of the connection of the main shaft, distal inner and outer tubes and insert of the balloon catheter of the present invention.

FIG. 3 shows in detail insert 16, which is preferably a metallic or polyimide tubing and which provides a platform for connecting main shaft 12 and distal outer and inner tubes 14 and 18. Insert 16 also provides a fluid path between lumen 24 and distal inflation lumen 26. FIG. 3 is a magnified view of a section of FIG. 1B showing in further detail main shaft 12, distal outer tube 14, insert 16, distal inner tube 18, guide wire 22, lumen 24 of main shaft 12, distal inflation lumen 26, main shaft/distal outer tube/insert bond 34, fluid path 36 of insert 16, and distal guide wire lumen 38.

FIG. 3 shows in greater detail how main shaft 12 and distal outer tube 14 are connected, and how insert 16 provides a platform and a fluid path between main shaft lumen 24 and distal inflation lumen 26. The distal end of main shaft 12 is bonded to the proximal end of distal outer tube 14 at bond 34. Insert 16 acts as a platform for bond 34 to support the connection between main shaft 12 and distal outer tube 14. The inner surface of main shaft 12 and the inner surface of distal outer tube 14 are bonded to the outer surface of insert 16 at bond 34. Insert 16 includes fluid path 36 which provides a flow path for fluid between main shaft lumen 24 and distal inflation lumen 26. An inner surface of insert 16 is bonded to the outer surface of distal inner tube 18. A proximal end of distal inner tube 18 is located at insert 16 and extends through distal outer shaft 14 and balloon member 20. A distal end of distal inner shaft 18 is connected to the distal end of balloon member 20, as seen in FIG. 1B.

As is shown in greater detail in FIG. 3, guide wire 22 extends through lumen 24 of main shaft 12 and distal guide wire lumen 38 of distal inner tube 18, and out the distal end of catheter 10. The inner diameter of distal inner tube 18 and the outer diameter of guide wire 22 are closely matched so that guide wire 22 occupies most of the cross-sectional area of guide wire lumen 38, leaving only a small fluid path within lumen 38. The fluid resistance of guide wire lumen 38, when guide wire 22 is extending through it, is far greater (e.g., about 50 times greater) than the fluid resistance from lumen 24 through insert 16 and distal inflation lumen 26 to the interior of balloon 20. This configuration allows for inflation/deflation without perceptible fluid flowing out the distal end of distal guide wire lumen 38 during inflation (pressurization through manifold 21), and without perceptible passage of fluid (blood) into lumen 38 and/or lumen 24 during deflation (vacuum applied through manifold 21.)

With the dilatation catheter 10 of the present invention, there is in effect a proximal single lumen portion (main shaft 12) and a distal multiple lumen portion (formed by distal outer tube 14 and distal inner tube 18). Lumen 24 of main shaft 12 functions as a combined inflation and guide wire lumen to which both distal inflation lumen 26 and a distal guide wire lumen 38 are connected. The present invention allows the catheter 10 to have a smaller outer diameter because of using only a single lumen proximally while retaining the advantages of an over-the-wire catheter due to the multilumen distal portion. This is accomplished by providing a fluid flow path between the combined lumen 24 and the interior of balloon 20 which has a much lower fluid resistance than there is through the distal guide wire lumen 38 when guide wire 22 is in place. The fluid flow resistance differential is a result of difference in cross-sectional area of the inflation lumen and the guide wire lumen for fluid flow, and from the fact that the much smaller guide wire lumen cross-sectional area extends longitudinally much further than the larger inflation lumen.

In the embodiment shown in FIGS. 1A, 1B, 2 and 3, distal outer tube 14 is preferably made of a flexible polymeric material such as high density polyethylene (HDPE), and has an inner diameter of about 0.026 inch, and an outer diameter of about 0.032 inch. Distal inner tube 18 is preferably a flexible polymeric material such as polyimide and has an inner diameter of about 0.012 inch, and an outer diameter of about 0.014 inch with a lubricious inner surface, such as a polyimide-polytetrafluoroethylene composite material.

In the following discussion and in FIGS. 4A–13, various embodiments of the present invention are shown which illustrate different ways in which a connection between a single lumen proximal portion and a multilumen distal portion can be made in accordance with the present invention.

Figure 4A:
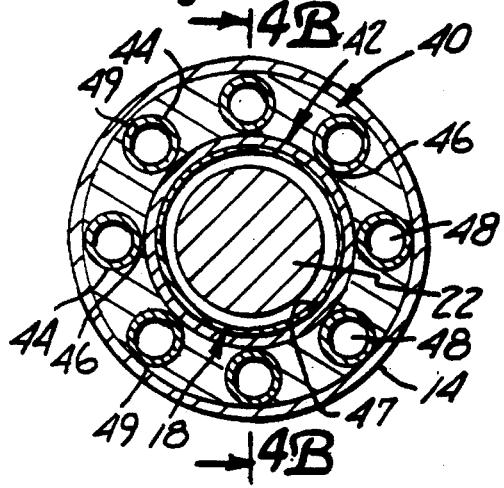
FIG. 4A is a detail lateral sectional view showing one preferred embodiment of the insert of the balloon catheter of the present invention.
Figure 4B:
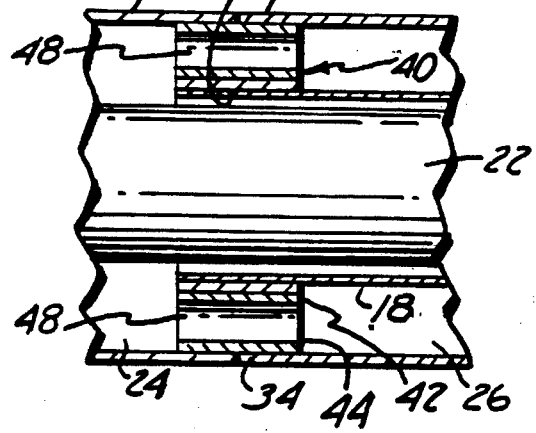
FIG. 4B is a sectional view along lines 4B—4B in FIG. 4A.

FIG. 4A is a front view showing wall insert 40 which includes main tubular member 42, a plurality of circumferentially spaced small diameter tubes 44, and bond 46. FIG. 4B is a sectional plan view of insert 40 shown in FIG. 4A. In this preferred embodiment of the present invention, the plurality of smaller diameter tubes 44 are bonded by bond 46 to an outer surface of main tubular member 42. Inner surface 47 of main tubular member 42 is bonded to distal inner shaft 18 shown in FIGS. 1, 2 and 3. Smaller diameter tubes 44 have channels 48 throughout their length which form a fluid path for the inflation medium (from lumen 24 of main shaft 12 to inflation lumen 26). Main tube 12 and distal outer shaft 14 shown in FIGS. 1, 2 and 3, are bonded by bond 49 to small diameter tubes 44 at a point located furthest from the axis of wall insert 40 on an outer surface of small diameter tubes 44. In this preferred embodiment, wall insert 40 is composed of metallic or polymeric tubes 44 that have a length of about 0.25 inch, and are bonded to a main tubular member 42 that has an inner diameter of about 0.015 inch, and an outer diameter of about 0.0165 inch.

Figure 5A:
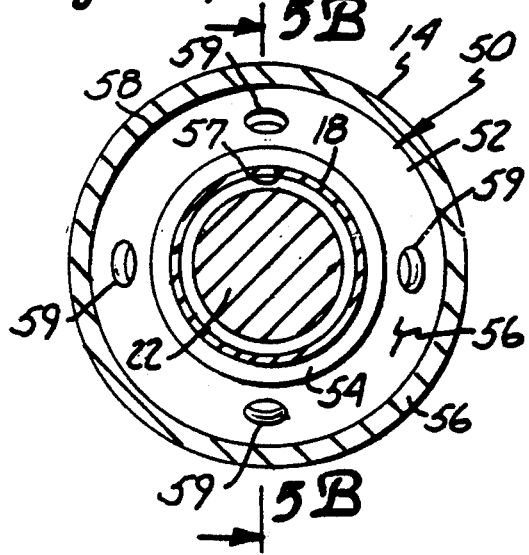
FIG. 5A is a detail lateral sectional view of an insert used in another preferred embodiment of the balloon catheter of the present invention.
Figure 5B:
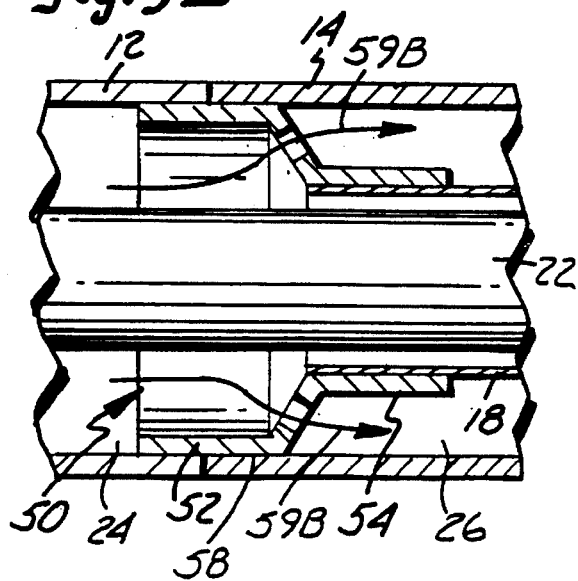
FIG. 5B is a sectional view along lines 5B—5B in FIG. 5A.

FIGS. 5A and 5B show insert 50, which is another preferred embodiment of the balloon catheter of the present invention. FIG. 5A is a front view of insert 50, showing proximal insert end 52, distal insert end 54, and transition region 56. Distal inner tube 18 is bonded to inner bond surface 57 of distal insert end 54, while main shaft 12 and distal outer tube 14 are bonded to outer bond surface 58 of proximal insert end 52 (which has a larger diameter than distal insert end 54). In this preferred embodiment, proximal insert end 52 has an inner surface diameter of about 0.025 inch, and an outer surface diameter of about 0.028 inch. Distal insert end 54 has an inside surface diameter of about 0.015 inch, and an outer surface diameter of about 0.018 inch. Insert 50 is preferably made of a metallic or polymeric material, and has a plurality of radial perforations 59 in transition region 56 which form a fluid path for inflation fluid (as illustrated by arrows 59A in FIG. 5B) between lumen 24 of main shaft 12 and inflation lumen 26. Radial perforations 59 need not be circular, and are located in the walls of transition region 56, where a diametrical transition occurs between proximal insert end 52 and distal insert end 54.

FIGS. 6A and 6B show ring-shaped insert 60, which is another preferred embodiment of the present invention. FIG. 6A is a front view of insert 60, which in this embodiment includes a plurality of circumferentially spaced, axially extending holes 62 which define fluid paths through insert 60. Insert 60 is bonded to distal inner shaft 18 at inner surface 66, and is bonded to main shaft 12 and distal outer tube 14 at outer surface 68.

FIG. 7 shows an embodiment in which insert region 70 is an integral portion of main shaft 12 at the distal thereof. Insert 70 includes a first proximal region 72 of reduced diameter, a second transition region 74 and a third distal end region 76. Distal outer tube 14 is bonded to an outer surface 73 of first region 72, while distal inner tube 18 is bonded to an inner surface 75 of third region 76. A plurality of holes 78 in second transition region 74 provide a fluid path through insert region 70 at the distal end of the main shaft 12.

FIG. 8 shows integral insert region 80 similar to insert 70 shown in FIG. 7, except that main shaft 12, distal inner tube 18, and insert region 80 are an integral unit. A plurality of holes 82 in insert region 80 provide the fluid path through insert region 80. In this embodiment, outer tube 14 is bonded to insert region 80 at bond 84, adjacent the transition portion of insert region 80 between main shaft 12 and distal inner tube 18.

In the embodiments of the present invention shown in FIGS. 5, 7 and 8, the insert has a region of generally progressive diametrical reduction between its proximal and distal regions (e.g., transition region 56 in FIGS. 5A and 5B and transition region 74 in FIG. 7) which aids in defining the guide wire lumen for the balloon catheter. Thus, when longitudinally inserting a guide wire into the balloon catheter of the present invention, a distal end of the guide wire 22 will be gently led or guided radially inwardly when it contacts the sloped walls of this transition region toward the opening for the distal guide wire lumen 38 at a proximal end of the distal inner tube 18.

Figure 9:
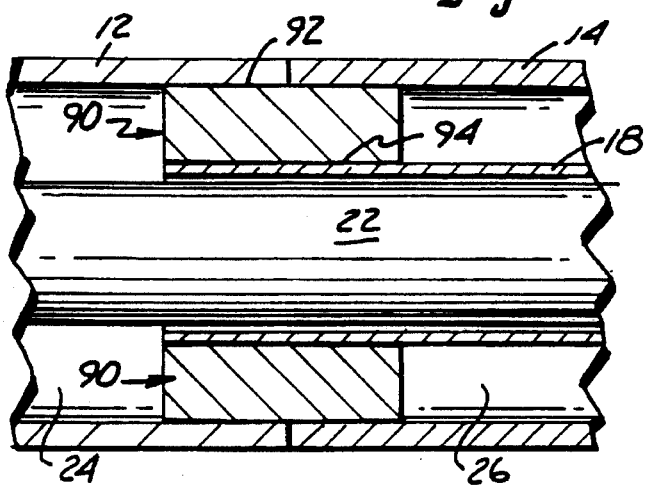
FIG. 9 is a detail sectional view of another preferred embodiment of the balloon catheter of the present invention.

FIG. 9 shows insert 90 formed by a ring of porous or permeable material. Main shaft 12 and distal outer tube 14 are bonded to outer surface 92 of insert 90, while distal inner tube 18 is bonded to inner surface 94 thereof. The fluid path between lumen 24 of main shaft 12 and inflation lumen 26 is through the porous material of insert 90.

Figure 10:
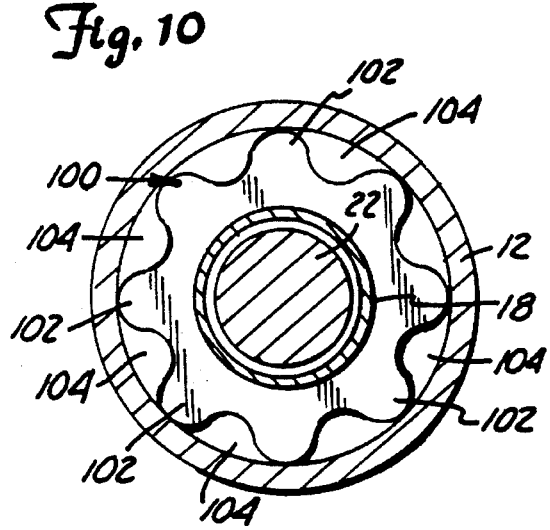
FIG. 10 is a detail lateral sectional view of an insert which is another preferred embodiment of the balloon catheter of the present invention.
Figure 12:
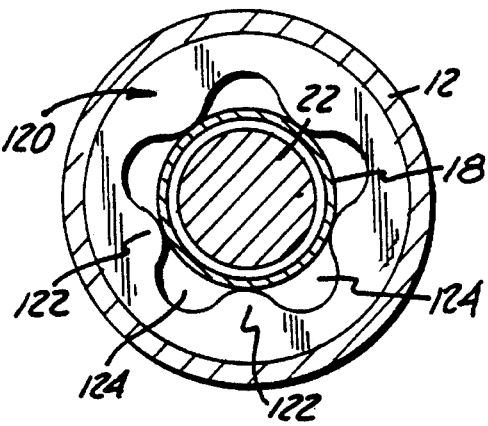
FIG. 12 is a detail lateral sectional view of an insert which is another preferred embodiment of the balloon catheter of the present invention.
Figure 11:
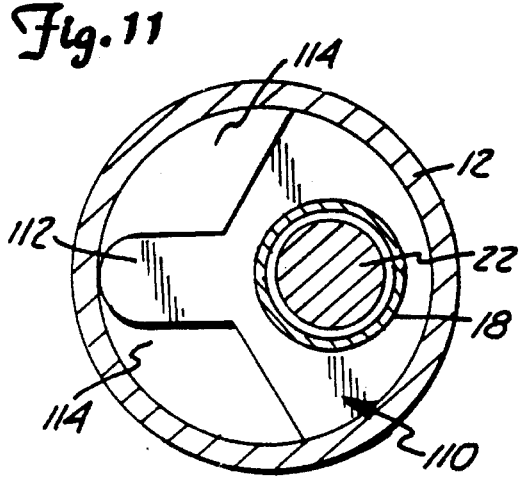
FIG. 11 is a detail lateral sectional view of an insert which is another preferred embodiment of the balloon catheter of the present invention.
Figure 13:
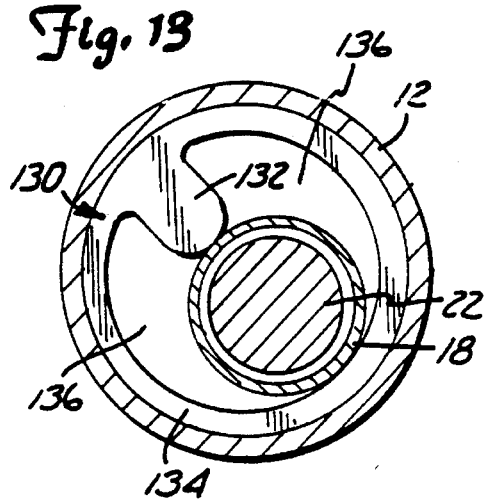
FIG. 13 is a detail lateral sectional view of an insert which is another preferred embodiment of the balloon catheter of the present invention.

FIGS. 10–13 show various ribbed or fluted insert shapes. Insert 100 shown in FIG. 10 is a multi-ribbed insert, an annular inner surface which mates with an outer surface of distal inner tube 18, and a plurality of exterior ribs 102 which define fluid paths 104 between insert 100 and shaft 12 (and distal outer tube 14). Insert 110 in FIG. 11 has a single exterior rib 112 which defines a pair of fluid paths 114 between insert 110 and shaft 12 (and distal outer tube 14). Insert 120 of FIG. 12 has an annular outer surface which mates with an inner surface of shaft 12 (and distal outer tube 14), and a plurality of inwardly projecting ribs 122 which define a plurality of fluid paths 124 between insert 120 and distal inner tube 18. Insert 130 in FIG. 13 has a single rib 132 projecting inwardly from an outer ring portion 134. Distal inner tube 18 is bonded between rib 132 and an inner wall of ring 134, and thus, a pair of fluid paths 136 are defined on opposite sides of rib 132 between the distal inner tube 18 and inner wall of ring 134.

The present invention offers the advantages of a single lumen catheter (primarily, reduced cross-sectional diameter) and a multiple lumen catheter (separate lumens for guide wire and inflation, thereby allowing catheter exchanges with the guide wire in place) in the same dilatation catheter. This is achieved by a single lumen proximal portion to which is attached a multilumen distal portion. Reduced shaft diameter for the main shaft of the dilatation catheter is achieved, while also obtaining the benefits of an over-the-wire arrangement due to the multilumen distal portion.

Although the present invention has been described with reference to preferred embodiments, workers skilled in the art will recognize that changes may be made in form and detail without departing from the spirit and scope of the invention.

What is claimed is:

1. A balloon catheter for use with a guide wire, the catheter comprising:

an outer tube having a proximal end and a distal end defining a length therebetween, the outer tube defining a single lumen therethrough wherein the single lumen extends the length of the outer the, said single lumen comprising an inflation lumen;

an inflatable balloon having a proximal end and a distal end, the proximal end of the balloon being connected to the distal end of the outer tube to extend distally therefrom, with the interior of the balloon in fluid communication with the inflation lumen; and an inner tube having a proximal end and a distal end and defining a guide wire lumen therethrough wherein the inner tube is disposed within the inflation lumen of the outer tube, the distal end of the inner tube being sealably connected to the distal end of the balloon, and the inner tube extending through the interior of the balloon so that the proximal end of the inner tube is proximal of the proximal end of the balloon, the inner tube being connected to the outer tube at a position substantially spaced distally from the proximal end of the outer tube, the inner tube further having an exterior surface which is radially displaced from an interior surface of the outer tube at the position of the connection between the inner tube and the outer tube.

2. A balloon catheter according to claim 1 wherein said inner tube is connected to the outer tube at a position which is closer to the distal end of the outer tube than to the proximal end of the outer tube.

3. A balloon catheter according to claim 2 further comprising a transition region which includes a proximal portion formed integrally with the outer tube, and a distal portion sealably connected to the inner tube for connecting the inner tube to the outer tube.

* * * * *

UNITED STATES PATENT AND TRADEMARK OFFICE
CERTIFICATE OF CORRECTION

PATENT NO. : 5,476,477
DATED : December 19, 1995
INVENTOR(S) : Matthew M. Burns

It is certified that error appears in the above-identified patent and that said Letters Patent is hereby corrected as shown below:

On the title page, item [73] should read
Assignee: SciMed Life Systems, Inc.

Col. 4, line 38, "TELFON", should be --TEFLON--.

Col. 6, line 48, "about0.025", should be --about 0.025--.

Col. 8, line 23, "extends the length of the outer the", should be
--extends the length of the outer tube--.

Signed and Sealed this

Thirtieth Day of April, 1996

*Attest:*

BRUCE LEHMAN

*Attesting Officer*  *Commissioner of Patents and Trademarks*